(12) United States Patent
Yamamoto et al.

(10) Patent No.: US 8,388,539 B2
(45) Date of Patent: Mar. 5, 2013

(54) OPERATION SUPPORTING DEVICE, METHOD, AND PROGRAM

(75) Inventors: Seiji Yamamoto, Shizuoka (JP);
Susumu Terakawa, Shizuoka (JP);
Toshihisa Takai, Shizuoka (JP);
Katsuhiro Sato, Shizuoka (JP); Keiichi Abe, Aichi (JP); Baigalmaa Tsagaan, Shizuoka (JP)

(73) Assignees: National University Corporation Hamamatsu University School of Medicine, Shizuoka (JP); National University Corporation Shizuoka University, Shizuoka (JP)

( * ) Notice: Subject to any disclaimer, the term of this patent is extended or adjusted under 35 U.S.C. 154(b) by 0 days.

(21) Appl. No.: 13/076,062

(22) Filed: Mar. 30, 2011

(65) Prior Publication Data

US 2012/0010498 A1    Jan. 12, 2012

Related U.S. Application Data

(63) Continuation of application No. 10/599,487, filed on Sep. 29, 2006.

(30) Foreign Application Priority Data

Mar. 30, 2004  (JP) .................................. 2004-099297
Mar. 29, 2005  (WO) .................. PCT/JP2005/005855

(51) Int. Cl.
*A61B 8/00* (2006.01)
(52) U.S. Cl. ........ 600/443; 600/407; 600/437; 600/424; 600/425; 600/427; 382/131
(58) Field of Classification Search .................. 600/437, 600/443, 424, 425, 427, 429; 382/131
See application file for complete search history.

(56) References Cited

U.S. PATENT DOCUMENTS

| 5,999,840 A | 12/1999 | Grimson et al. |
| 6,106,464 A | 8/2000 | Bass et al. |
| 6,347,240 B1 | 2/2002 | Foley et al. |
| 6,557,558 B1 | 5/2003 | Tajima et al. |

(Continued)

FOREIGN PATENT DOCUMENTS

| JP | 2000333971 | 12/2000 |
| JP | 2001061860 | 3/2001 |

(Continued)

OTHER PUBLICATIONS

Non Final Office Action regarding U.S. Appl. No. 10/599,487, issued Aug. 4, 2011, 11 pages.
Ferrant, M. et al, Registration of 3-D Intraoperative MR Images of the Brain Using a Finite-element Biomechanical Model, Transactions on Medical Imaging, 2001, pp. 1384-1397, vol. 20, No. 12.
European Search Report dated Sep. 1, 2009 regarding Application No. EP05727540, three (3) pages.

(Continued)

*Primary Examiner* — Unsu Jung
*Assistant Examiner* — Joseph M Santos
(74) *Attorney, Agent, or Firm* — Polsinelli Shughart PC

(57) ABSTRACT

Surgical operation supporting apparatus and method is disclosed in which based on a high-definition tomographic images of an operation site produced before surgery, a three-dimensional model of the operation site is generated, and a surface of the operation site is optically measured during the surgical operation, and further, first position information that represents a three-dimensional position of each of points on the surface is acquired. An unexposed portion of the operation site is measured with ultrasonic waves during the surgical operation, and second position information that represents a three-dimensional position of each of points in the unexposed portion is acquired. Based on the first position information and the second position information, displacement and distortion at a portion whose three-dimensional position is not known in the three-dimensional model is estimated to obtain an estimated result. The three-dimensional model is re-corrected by use of a finite element method and the estimated result.

10 Claims, 6 Drawing Sheets

U.S. PATENT DOCUMENTS

| | | |
|---|---|---|
| 6,681,129 B2 | 1/2004 | Matsuzaki et al. |
| 6,895,268 B1 | 5/2005 | Rahn et al. |
| 6,950,689 B1 | 9/2005 | Willis et al. |
| 2001/0016684 A1 | 8/2001 | Shahidi |
| 2002/0042566 A1 | 4/2002 | Matsuzaki et al. |
| 2005/0101855 A1 | 5/2005 | Miga et al. |

FOREIGN PATENT DOCUMENTS

| | | |
|---|---|---|
| JP | 2001061861 | 3/2001 |
| JP | 2002102249 | 4/2002 |
| JP | 2002522106 T | 7/2002 |
| JP | 2003109042 | 4/2003 |
| WO | 0187136 | 11/2001 |

OTHER PUBLICATIONS

Nakao, M et al, An Adaptive Physics-Based Framework Enabling Cutting and Deformation for Virtual Bodies, Jyohoshori Gakkai Zenkoku Taikai Koen Ronbun Shu, (paper collection of Information Processing Society of Japan (IPSJ) National Convention Report, Japan, Mar. 35, 2003, pp. 379-382, vol. 65, No. 5(5). (Japanese translation).

Nakao, M et al, An Adaptive Physics-Based Framework Enabling Cutting and Deformation for Virtual Bodies, Jyohoshori Gakkai Zenkoku Taikai Koen Ronbun Shu, (paper collection of Information Processing Society of Japan (IPSJ) National Convention Report, Japan, Mar. 35, 2003, pp. 379-382, vol. 65, No. 5(5). (English translation).

CROSS-SECTIONS INTENDED FOR PICKUP IMAGES BY MRI

BRAIN

FRONT

LEFT　　　　RIGHT

SKIN CUT OPEN LINE

RANGE FOR CRANIAL SURGERY (REMOVAL OF BONES)

MRI IMAGES

⇒

3-D BRAIN MODEL

F I G. 6 A
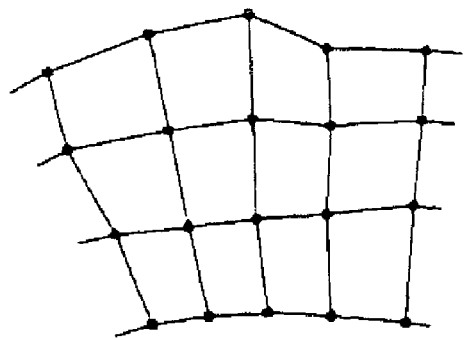
F I G. 6 B
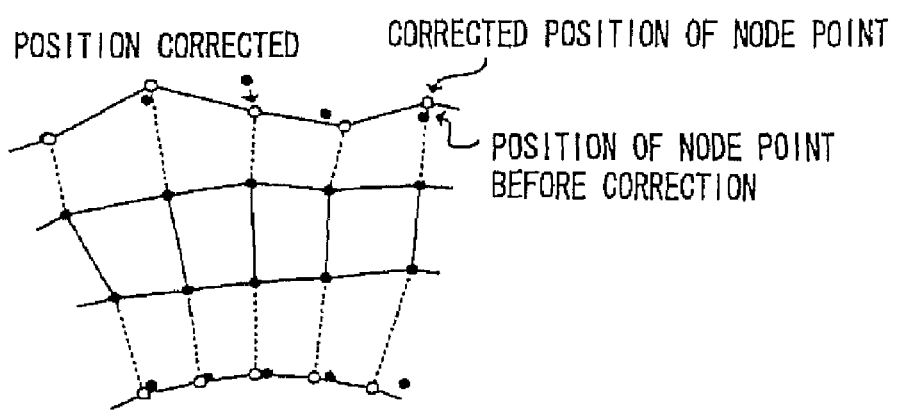
POSITION CORRECTED    CORRECTED POSITION OF NODE POINT
POSITION OF NODE POINT BEFORE CORRECTION
F I G. 6 C
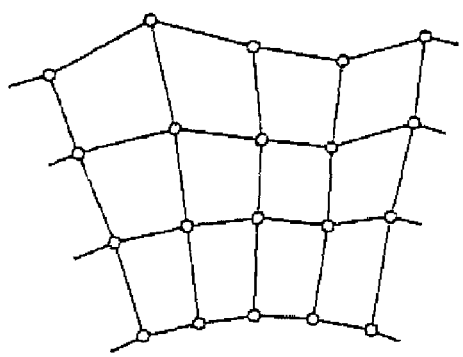

US 8,388,539 B2

OPERATION SUPPORTING DEVICE, METHOD, AND PROGRAM

RELATED APPLICATIONS

This application is a continuation of U.S. patent application Ser. No. 10/599,487, filed Sep. 29, 2006, and entitled Operation Supporting Device, Method and Program, which is related to International Patent Application No. PCT/JP2005/005855, filed Mar. 29, 2005, and entitled Operation Supporting Device, Method and Program, and which both take priority to Japanese Patent Application No., 2004-099297, filed Mar. 30, 2004, and entitled Operation Supporting Device, Method and Program, the entire contents of which are incorporated herein by reference.

TECHNICAL FIELD

The present invention relates to a surgical operation supporting apparatus, method and program, and particularly to a surgical operation supporting apparatus and method that supports a surgical operation by correcting a plurality of high-definition tomographic images of an operation site) which images are picked up before surgery, and by displaying these images on display means, and also to a surgical operation supporting program used to allow a computer to function as the surgical operation supporting apparatus.

BACKGROUND OF THE ART

Nuclear magnetic resonance-computed tomography (occasionally referred to as MRI (Magnetic Resonance Imaging) or NMR-CT (Nuclear Magnetic Resonance-Computed Tomography)) is used to obtain tomographic images of a living body by utilizing a nuclear magnetic resonance phenomenon of an atomic nucleus having spin in the living body within the static magnetic field. The aforementioned tomography has features of avoiding radiation exposure as in X-ray CT imaging, being free of influence from the bones, providing high-definition tomographic images along an arbitrary direction, and so on, and therefore, it is used in various medical fields such as surgery and resting (tomographic images obtained by the nuclear magnetic resonance-computed tomography will be hereinafter referred to as MRI images).

For example, the boundary between a brain tumor to be removed in an operation of cranial nerve surgery, and a healthy portion is not clearly recognized in a visual observation manner. Therefore, in the operation of cranial nerve surgery, MRI images of the head region are taken in advance, and an actual operation site are compared with the MRI images of the head region in a repeated manner. Thus, the surgical operation is proceeded while making a diagnosis of the boundary between the brain tumor and the healthy portion. Further, a human's brain includes functionally critical areas (eloquent areas, for example, a pyramidal area, a sensory area, a linguistic area, a visual area, an auditory area, and so on). Thus, distribution of these eloquent areas in what place and in what manner is inspected in advance and the state in which various eloquent areas are distributed is displayed as a map on an MRI image of the head region referred to during the surgery (which map is occasionally referred to as a functional mapping MRI).

In conjunction with the foregoing, the non-patent document 1 discloses an optical surgery navigation apparatus that is constructed in such a manner that in the operation of cranial nerve surgery, an MRI image of the head region taken before surgery, and a space of an operation site are made to correspond to each other using a common coordinate system due to a position detector using infrared light, and the position of a region for which a surgical operation is currently performed is detected and shown on the MRI image.

Further, the non-patent document 2 discloses a navigation apparatus that is constructed in such a manner that ultrasonic tomographic images are picked up by an ultrasonic probe during surgery, and the position of the ultrasonic probe is detected by infrared light, thereby causing an MRI image of the head region taken before surgery to correspond to the ultrasonic tomographic images taken during surgery, and in the same manner as in the optical surgery navigation apparatus as disclosed in the non-patent document 1, an operative region for which the surgical operation is currently performed is shown on the MRI image.

Further, the patent document 1 discloses the technique that the position and orientation of a surgical microscope are detected by an optical position measurement system, data processing of enlargement ratio, focal distance and so on is carried out, and image information such as MRI images of the head region, cerebral images and so on is superimpose-displayed in such a manner as to be aligned with real-time images taken by a surgical microscope during surgery, Moreover, the patent document 2 discloses the technique that a high-definition MRI image taken before surgery (a preoperative image) is reconfigured into a three-dimensional image, and the three-dimensional image is distorted based on a deformation condition for estimated distortions, and is stored as deformation data, and further, an MRI image is taken during surgery, and a two-dimensional image of an area of interest in the preoperative image is reconfigured into a three-dimensional image, and the similarity to the deformation data is calculated and optimum deformation data is selected, and an image of an object from a calibration mirror is superimpose-displayed thereon.

Patent document 1. JP-A No. 2000-333971
Patent document 2: JP-A No. 2002-102249

DISCLOSURE OF THE INVENTION

Problems to be Solved by the Invention

However, in the operation of cranial nerve surgery, a brain of a patient is distorted during the surgical operation. Therefore, it is difficult for a surgeon to make a diagnosis of an actual brain condition (for example, the position or area of a brain tumor) during surgery with a high degree of accuracy even if the surgeon refers to an MRI image of the head region taken before the surgical operation. Any of the aforementioned non-patent documents 1 and 2, and patent document 1 gives no consideration to distortions of the brain caused by the surgical operation, and each disclose the technique that new information is added to the MRI image taken before surgery or an MRI image is aligned with a real-time image. Thus, these techniques would become helpful to the surgery, but do not necessarily contribute to improvement of the precision of the surgery.

The aforementioned problem can be solved by carrying out pickup of an MRI image at fixed intervals during surgery and updating the MRI image used for reference during surgery at regular intervals, as in the technique disclosed in the patent document 2 or the like. However, in order to realize this solving method, it is necessary to install an MRI imaging device in an operating room, and also necessary to use surgical equipment and materials made of non-magnetic materials, and so on. This result in an extremely high cost and many restrictions. Further, a fresh problem arises in which the surgical operation needs to be stopped during a pickup operation of MRI images. Moreover, the technique disclosed in the patent document 2 also has a disadvantage that when distortions of an operation site during the surgery differ from the estimated deformation condition, the precision of a displayed image deteriorates.

The present invention has been achieved in view of the aforementioned circumstances, and an object of the present invention is to provide a surgical operation supporting apparatus, a surgical operation supporting method and a surgical operation supporting program, which each can realize presentation of images using a simple structure, which images represent a state of an operation site during surgery with a high degree of accuracy.

Means for Solving the Problems

According to a first aspect of the present invention, there is provided a surgical operation supporting apparatus comprising: first acquisition means that optically measures a surface of an operation site during surgery and that acquires first position information representing a three-dimensional position of each of points on the surface of the operation site; second acquisition means that measures an unexposed portion of the operation site with ultrasonic waves during surgery and that acquires second position information representing a three-dimensional position of each of points in the unexposed portion of the operation site; correction means that, based on the first position information acquired by said first acquisition means and the second position information acquired by said second acquisition means, estimates displacement and distortion at each of the points in the operation site using a three-dimensional model generated based on a plurality of high-definition tomographic images of the operation site, which images are taken before surgery, and that corrects the plurality of high-definition tomographic images; and display control means that allows the high-definition tomographic images corrected by said correction means to be shown on display means.

According to a second aspect of the present invention, there is provided a surgical operation supporting method comprising: a first step in which based on a plurality of high-definition tomographic images of an operation site taken as an image before surgery, a three-dimensional model of the operation site is generated a second step in which a surface of the operation site is optically measured during surgery, so as to acquire first position information that represents a three-dimensional position of each of points oil the surface of the operation site, and an unexposed portion of the operation site is measured with ultrasonic waves during surgery, so as to acquire second position information that represents a three-dimensional position of each of points of the unexposed portion in the operation site; a third step in which based on the first position information and the second position information acquired by said second step, displacement and distortion at each of the points in the operation site are estimated using the three-dimensional model generated by said first step, and in accordance with the estimated displacement and distortion at each of the points in the operation site, the plurality of high-definition tomographic images of the operation site taken as images before surgery are corrected; and a fourth step in which the high-definition tomographic images corrected by said third step are shown on display means.

According to a third aspect of the present invention, there is provided a surgical operation supporting program that causes a computer, to which display means is connected, to function as: first acquisition means that optically measures a surface of an operation site during surgery and that acquires first position information representing a three-dimensional position of each of points on the surface of the operation site; second acquisition means that measures an exposed portion of the operation site with ultrasonic waves during the surgery and that acquires second position information representing a three-dimensional position at each of points in the unexposed portion of the operation site; correction means that, based on the first position information acquired by said first acquisition means and the second position information acquired by said second acquisition means, estimates displacement and distortion at each of the points in the operation site using a three-dimensional model generated based on a plurality of high-definition tomographic images obtained before the surgery, and in accordance with the estimated displacement and distortion occurring at each of the points in the operation site, corrects the plurality of high-definition tomographic images of the operation site, which images are produced before the surgery; and display control means that causes the high-definition tomographic images corrected by said correction means to be shown on display means.

EFFECTS OF THE INVENTION

According to the present invention, a surface of an operation site is optically measured during surgery and first position information representing a three-dimensional position of each of points on the surface of the operation site is acquired; an unexposed portion of the operation site is measured with ultrasonic waves during surgery and second position information representing a three-dimensional position of each of points in the unexposed portion of the operation site is acquired; based on the first position information and the second position information, displacement and distortion occurring at each of the points in the operation site are estimated using a three-dimensional model generated based on a plurality of high-definition tomographic images of the operation site, which images are taken before surgery, and the plurality of high-definition tomographic images are corrected; and the corrected high-definition tomographic images are shown on display means, thereby making it possible to produce an excellent effect that presentation of images each representing a state of an operation site during surgery with a high degree of accuracy can be realized using a simple structure.

BRIEF DESCRIPTION OF THE DRAWINGS

FIG. 6A is an image diagram for illustrating correction of a three-dimensional brain model based on three-dimensional coordinates of each of points on the surface of a brain and each of feature points corresponding to an unexposed portion of the brain, in which the three-dimensional brain model generated from MRI images is shown, in a simplified manner, as a two-dimensional one for purpose of easy viewing.

FIG. 6B is an image diagram for illustrating correction of a three-dimensional brain model based on three-dimensional coordinates of each of points on the surface of a brain and each of feature points corresponding to an unexposed portion of the brain, which diagram shows a three-dimensional brain model in which positions of corresponding node points are corrected based on the three-dimensional coordinates of each of points on the surface of the brain and each of feature points corresponding to the unexposed portion of the brain.

FIG. 6C is an image diagram for illustrating correction of a three-dimensional brain model based on three-dimensional coordinates of each of points on the surface of a brain and each of feature points corresponding to an unexposed portion of the brain, which diagram shows a three-dimensional brain model corrected by estimating and calculating positions of the node points whose positions are not corrected, using a finite element method, with a group of node points indicated by a parenthesis mark at the right side being that of node points whose positions are estimated and calculated using the finite element method.

BEST MODE FOR CARRYING OUT THE INVENTION

One of embodiments of the present invention will be described hereinafter in detail with reference to the attached drawings, In the following description, a case example is given when the present invention is applied to a surgical operation supporting system used to remove a brain tumor formed within a brain of a patient, which is an operation site, but the present invention is not limited thereto.

Figure 1:
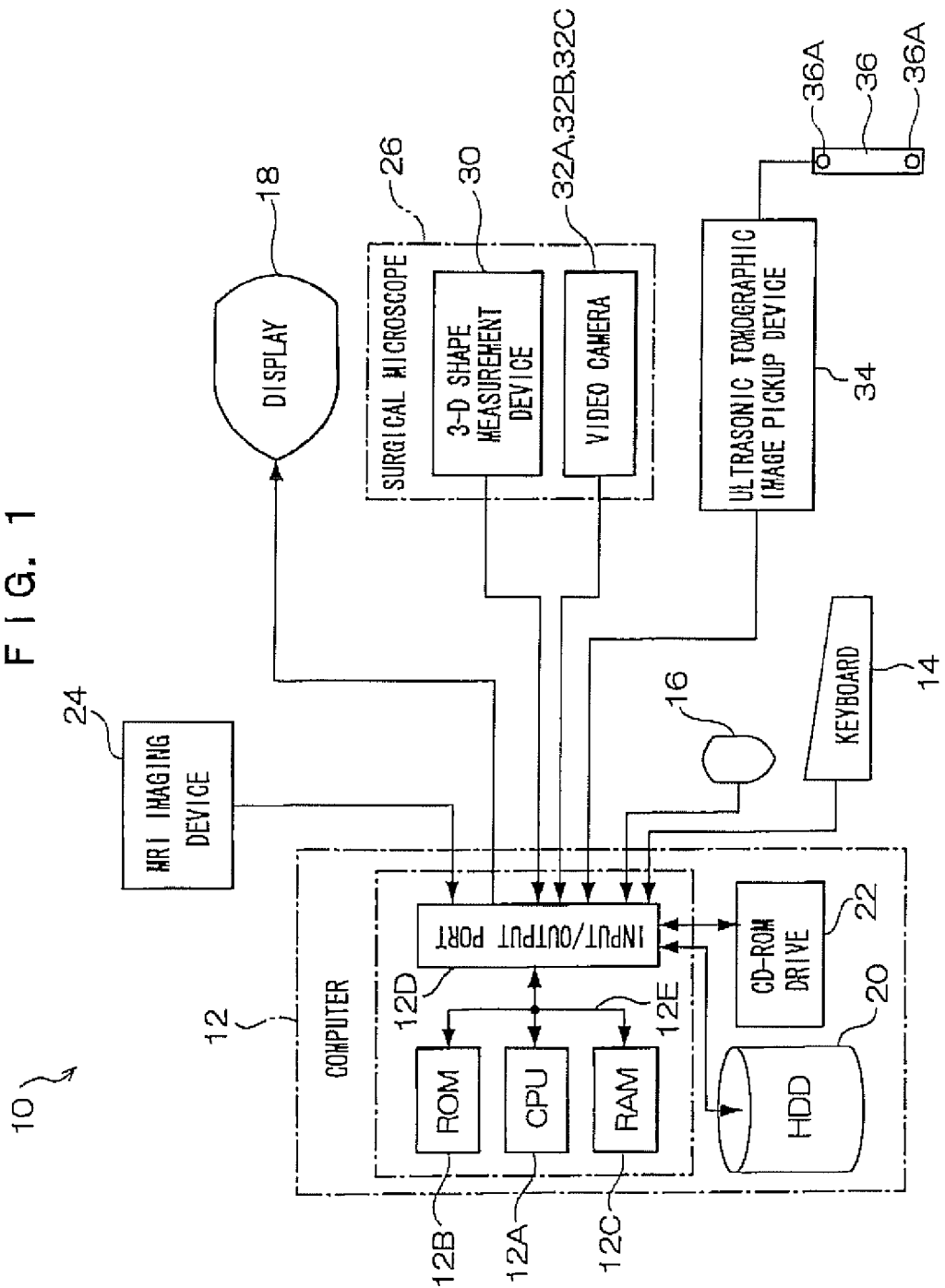
FIG. 1 is a block diagram schematically showing the structure of a surgical operation supporting apparatus.

FIG. 1 shows a surgical operation supporting apparatus 10 according to an embodiment of the invention, The surgical operation supporting apparatus 10 includes a computer 12 constituted from a personal computer (PC) and the like. The computer 12 includes CPU 12A, ROM 123, RAM 12C and an input/output port 12D and these components are connected with one another via a bus 12E. Further, connected to the input/output port 12D are a keyboard 14 and a mouse 16 which are used for a user to input arbitrary information or give various instructions, a display 18 comprised of LCD or CRT and allowing displaying of the arbitrary information, a hard disk drive (HDD) 20 and a CD-ROM drive 22, respectively. The display is corresponds to display means according to the present invention.

A three-dimensional model generation pro-ram for generating a three-dimensional brain model, which will be described later, and an MRI image display program for carrying out MRI image displaying processing which will be described later, are previously installed in the HDD 20 of the computer 12.

There are several methods for installing (introducing) the three-dimensional generation program and the MRI image display program into the computer 12. For example, a CD-ROM in which the three-dimensional model generation program and the MRI image display program are recorded together with a setup program is set in the CD-ROM device 22 of the computer 12, and when the CPU 12A receives an instruction to execute the setup program, the three-dimensional model generation program and the MRI image display program are sequentially read out from the CD-ROM and written in the HDD 20. Due to various types of setting being carried out if desired, installation of the three-dimensional model generation program and the MRI image display program is performed.

Further, connected to the input/output port 12D of the computer 12 are an MRI imaging device 24 that allows high-definition tomographic images (MRI images) of a living body to be taken in an arbitrary direction by the nuclear magnetic resonance-computed tomography, a three-dimensional shape measurement device 30 and a video camera 32, 32A, 32B, 32C which are attached to a surgical microscope 26, and an ultrasonic tomographic device 34 allows pickup of ultrasonic tomographic images of a living body, respectively. The MRI imaging device 24 is a image pickup device that carries out pickup of "a plurality of high-definition tomographic images for an operation site" according to the present invention before surgery, and is located in an MRI image pickup room provided separately from an operating room. Incidentally, when MRI image displaying processing, which will be described later, is executed by the computer 12, it suffices that MRI image data taken by the MRI image pickup device 24 before surgery can be acquired from the MRI image pickup device 24. Therefore, the computer 12 may not be connected to the MRI image pickup device 24, and MRI image data may also be transferred from the MRI image pickup device 24 to the computer 12 via any one of various recording media such as CD-R, CD-RW, MO, ZIP, DVD-R, DVD-RW and so on.

Figure 2A:
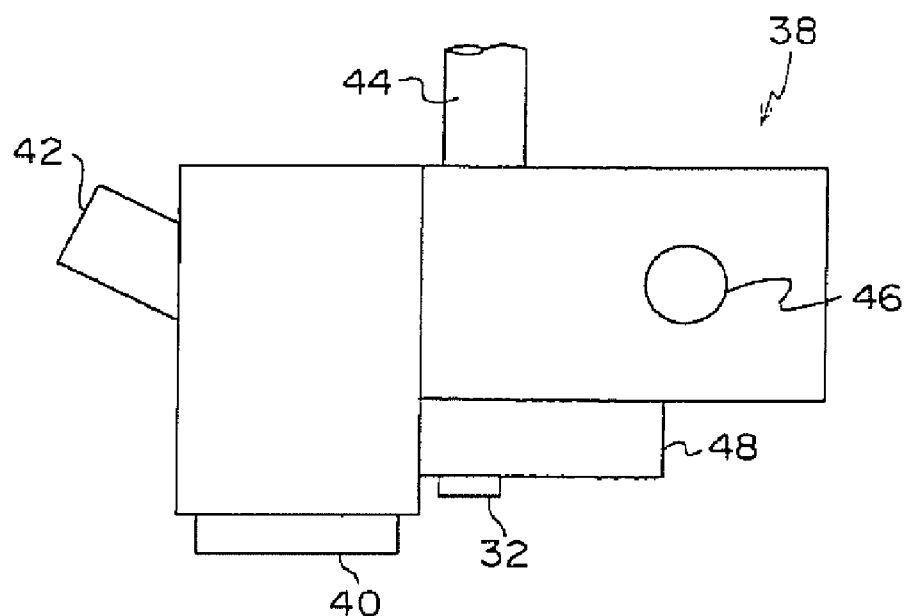
FIG. 2A is a side view of a surgical microscope equipped with a three-dimensional shape measurement device and a video camera.
Figure 2B:
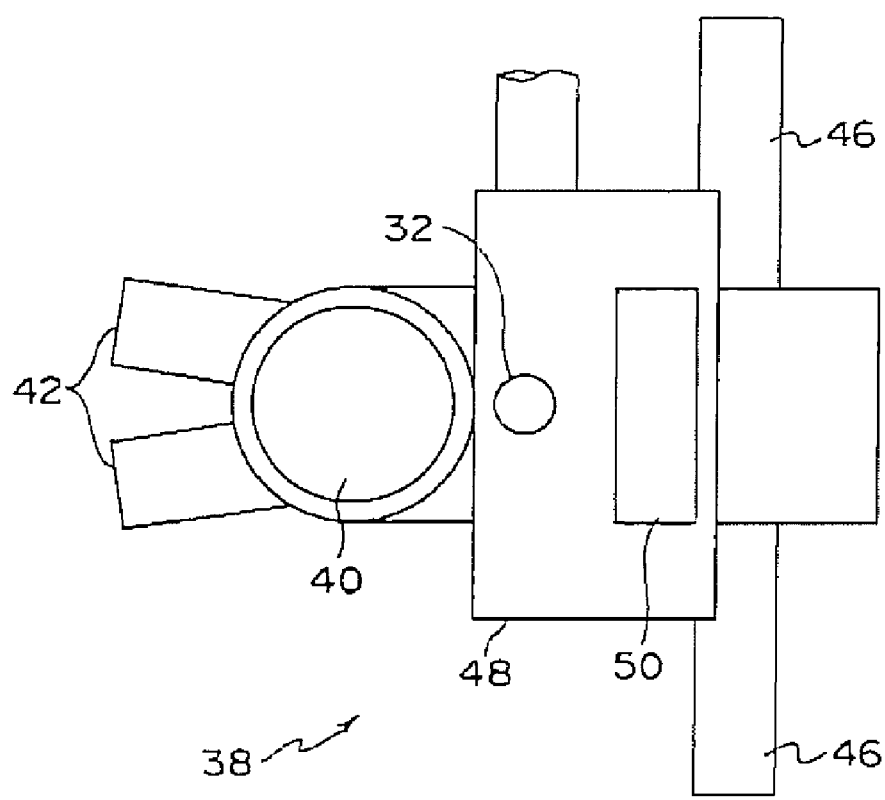
FIG. 2B is a bottom plan view of a surgical microscope equipped with a three-dimensional shape measurement device and a video camera.

The surgical microscope 26 includes a microscope portion 38 shown in FIG. 2. The microscope portion 38 is equipped with an objective lens 40 directed toward the lower side of the microscope portion 38 (to the lower side in FIG. 2(A)), and an eyepiece lens 42 disposed so as to project obliquely upward from the side surface of the microscope portion 38. The objective lens 40 is specifically a zoom lens (a focal distance variable lens) comprised of a plurality of lenses. Although not illustrated, optical components such as a prism that guides light incident on the objective lens 40 toward the eyepiece lens 42 are disposed between the objective lens 40 and the eyepiece lens 42. Thus, an optical image of an object formed by the objective lens 40 and the eyepiece lens 42 is visually recognized (stereoscopic viewing) by a surgeon that takes a look inside the eyepiece lens 42 with both eyes. A focusing mechanism is provided between the objective lens 40 and the eyepiece lens 42, and focusing and zooming of an optical image of the object is made adjustable by the surgeon operating a foot switch or a switch attached in the vicinity of a lens barrel of the microscope portion 38S.

The surgical microscope 26 includes a base portion fixed at a predetermined position within the operating room. One end of an arm 44 formed by connecting respective ends of plural rods in a rotatable manner is connected to the base portion in a rotatable manner. The microscope portion 38 is connected rotatably to the other end (a leading end) of the arm 44 (FIG. 2 shows only one end of the arm 44). An operating grip portion 46 is attached to the side surface of the microscope portion 38, and due to the surgeon holding the grip portion 46 to move the microscope portion 38, several connecting portions (joints) of the arm 44 are rotated so as to move the microscope portion 38 to a desired position or direct to a desired direction, thereby making it possible for a surgeon to visually recognize a desired visual field as an optical image.

Further, a measurement/image-pickup unit 48 having the three-dimensional shape measurement device 30 and the video camera 32 integrated therewith is mounted on the bottom surface of the microscope portion 38. The measurement/image-pickup unit 48 has a box-shaped case body, and the video camera 32 is attached to the case body of the measurement/image-pick unit 43 so as to allow imaging of the lower side of the microscope portion 38, Further, a rectangular opening is formed on the bottom surface of the case body of the measurement/image-pickup unit 48, and the opening is closed by a light transmission cover 50. The three-dimensional shape measurement device 30 is attached at a position corresponding to the cover 50 (opening) within the case body of the measurement/image-pickup unit 48.

Figure 3A:
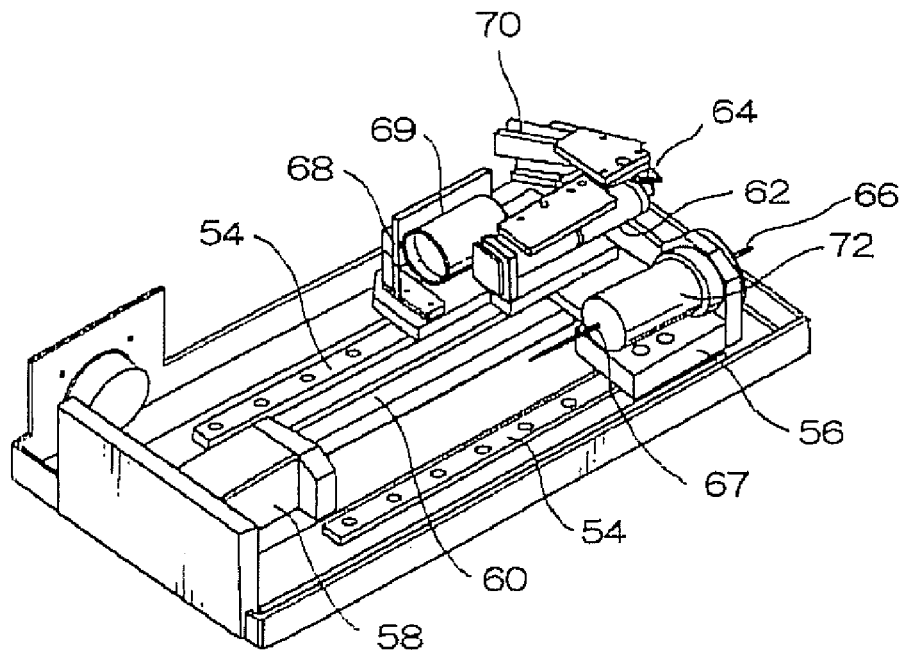
FIG. 3A is a perspective view showing an internal structure of the three-dimensional shape measurement device.
Figure 3B:
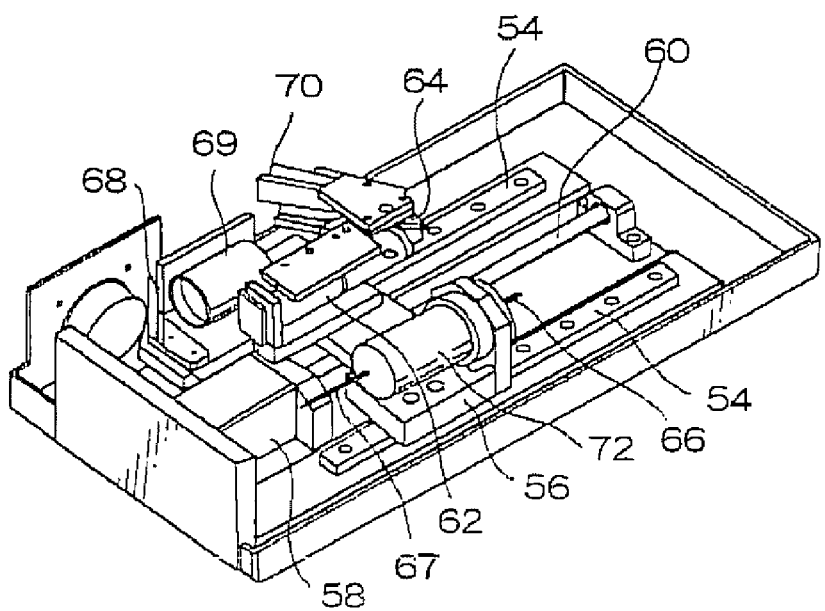
FIG. 3B is a perspective view showing an internal structure of the three-dimensional shape measurement device.

As shown in FIG. 3, the three-dimensional shape measurement device 30 is equipped with a movable base 56 straddling between a pair of rails 54. A ball screw 60 extending in parallel with the rails 54 and rotated by a motor 58 screws with the movable base 56, so that the movable base 55 is moved to slide along the rails 54 due to the rotation of the ball screw 60. Further, the movable base 56 is provided with a light emitting portion 62 including a laser light source. Disposed sequentially at the side from which laser light (outgoing laser light) is emitted from the light emitting portion 62 are a mirror 64 mounted on the movable base 56, and a galvanometer mirror 66 mounted on a rotating shaft of a motor 72 and turned over due to driving of the motor 72. The outgoing laser light emitted from the light emitting portion 62 is reflected by the mirror 64 and the galvanometer mirror 66, so as to be transmitted through the cover 50 and emitted out of the case body of the measurement/image-pickup unit 48.

Further, the outgoing laser light emitted out of the case body of the measurement/image-pickup unit 48 is reflected by an object to be irradiated (for example, the surface of a brain that is an operation site), and the reflected light, i.e., return laser light, is transmitted through the cover 50 and made incident on a mirror 67. The mirror 67 is mounted on the rotating shaft of the motor 72 along the same direction as that of the galvanometer mirror 66, and is constructed so that the direction thereof is changed due to the driving of the motor 72. Disposed sequentially at the side from which return laser light is emitted from the mirror 67 are a mirror 68, a lens 69 and a line sensor 70 having a large number of photoelectric transfer elements arranged in one row. The return laser light made incident on the mirror 67 is reflected by the mirrors 67 and 68 and made transparent through the laser 69, and subsequently received by the line sensor 70. An output signal from the line sensor 70 is inputted to a controller of the three-dimensional shape measurement device 30 via an amplifier or an A/D converter (which amplifier and A/D converter are both omitted in the drawings). Further, connected to the controller are a position sensor that detects the position of the movable base 56, and an angle sensor that detects the direction of the galvanometer mirror 66 (and the mirror 67).

The controller makes a determination as to whether laser light is received by which photoelectric transfer element of the line sensor 70 based on light-receiving data inputted from the line sensor 70 via the amplifier or A/D converter. And then, based on the position of the photoelectric transfer element having received laser light on the line sensor 70, the position of the movable base 56 detected by the sensor, and the direction of the galvanometer mirror 66, three-dimensional coordinates of a position on the object to be irradiated, at which laser light is irradiated (specifically, three-dimensional coordinates in a three-dimensional coordinate system set with the position of the case body of the measurement/image-pickup unit 48 serving as a reference (which coordinate system is referred to as a box type coordinate system)) is detected (calculated) using a triangulation method. Further, the motors 72 and 58 are each connected to the controller, and by driving the motor 72 to change the direction of the galvanometer mirror 66 (and the mirror 67), so as to allow the laser light irradiation position on the object to be irradiated to move along a direction orthogonal to the axis line of the rotating shaft of the motor 72 (main scan) and further by moving the motor 58 to move the movable base 56, the laser light irradiation position on the object to be irradiated is moved along a direction parallel to the rails 54 (sub-scan).

As a result, the surface configuration of the object to be irradiated (three-dimensional coordinates of each of spots on the surface of the object to be irradiated) is entirely measured by the three-dimensional shape measurement device 30. When tie three-dimensional shape measurement device 30 receives an instruction from the computer 12, the three-dimensional shape measurement device 30 carried out measurement of the surface configuration of the object to be irradiated, and outputs, to the computer 12, data representing three-dimensional coordinates of each spot on the surface of the object to be irradiated, which data is obtained by the measurement (such data is hereinafter referred to as surface measurement data). The surface measurement data corresponds to first position information according to the present invention. The rails 54, the movable base 56, the motor 58, the ball screw 60, the light emitting portion 62, the mirror 64, the galvanometer mirror 66 and the motor 72 collectively correspond to a scanning device as defined in claim 2, and the mirrors 67, 68, the lens 69, the line sensor 70 and the motor 72 collectively correspond to detecting means as defined in claim 2. Further, the position and direction of the video camera 32 are adjusted so as to allow imaging of the same area as that measured by the three-dimensional shape measurement device 30.

As also shown in FIG. 1, connected to the ultrasonic tomographic device 34 is a probe 36 that transmits ultrasonic waves and receives ultrasonic waves reflected by any object. The ultrasonic tomographic device 34 converts a sign 31 inputted from the probe 36 after the probe 36 receives the ultrasonic waves, to an ultrasonic tomographic image, and outputs the same to the computer 12. Further, the probe 36 includes marks 36A which are made from materials having a high light reflectivity, attached respectively at the leading end and the rear end thereof, so as to detect the position and direction of the probe 36. As will be described later, when ultrasonic tomographic images are taken by the ultrasonic tomographic device 34, the three-dimensional coordinates of the mark 36A attached to the probe 36 are measured by the three-dimensional shape measurement device 30.

Next, the operation of the present embodiment will be described. In the present embodiment when a surgical operation for removing a brain tumor is performed, first: MRI images of a head region of a patient (a patient targeted for the surgical operation) are taken in advance by the MRI imaging device 24 in the MRI imaging room. At the time of taking the MRI image, as shown in FIG. 4B, based on a skin cut line (a line that represents a position at which the scalp is cut open) which is determined in advance for the head region of the patient, three or more preoperative marks 80 comprised of materials coming out well in an MRI image are attached at the position in the head region of the patient can the periphery of an area to be cut open during surgery. The preoperative marks 80 correspond to first marks as defined in claim 8, and for example, spherical type white marks of approximately 5 mm in diameter can be used. Incidentally, the area for which cranial surgery is performed, as shown in FIG. 4B, represents an area in which a portion of the skull is removed during surgery.

Figure 4A:
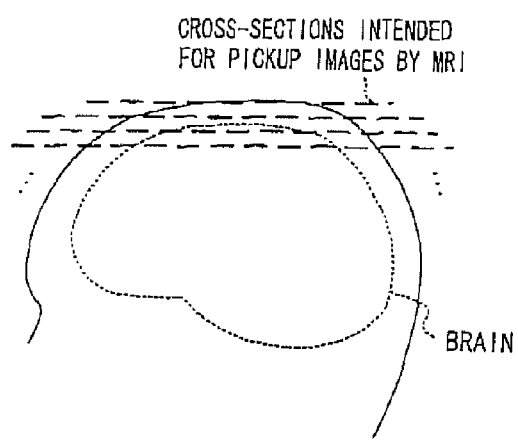
FIG. 4A is an image diagram for illustrating pickup of MRI images and generation of a three-dimensional brain model from the MRI images.
Figure 4B:
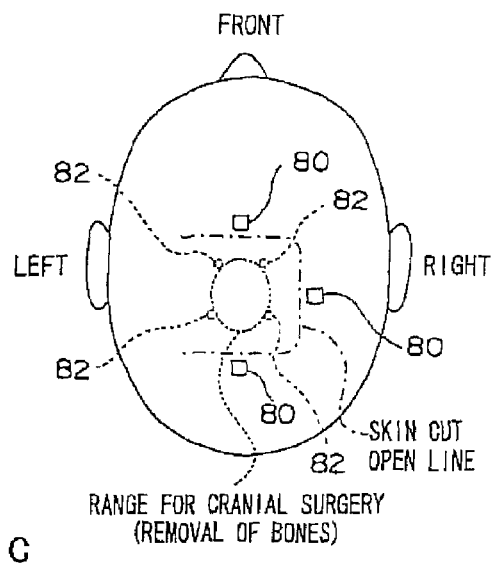
FIG. 4B is an image diagram for illustrating pickup of MRI images and generation of a three-dimensional brain model from the MRI images.

As shown in FIG. 4A for instance, an MRI image is taken by the MRI imaging device 24 for each of a plurality of cross-sections set at regular intervals (e.g., 1 mm or thereabouts) for the head region of the patient. As a result, a plurality of MRI images (a plurality of light-definition tomographic images at the operation site) in which the plurality of cross-sections are made visible with high degree of definition. Some of the plurality of MRI images obtained by the imaging process includes the preoperative marks 80 coming out therein. Further, the preoperative marks 80 applied to the head region of the patient remain unchanged from their attachment positions by the time of surgery. Moreover, the plurality of MRI images taken by the MRI imaging device 24 correspond to a plurality of high-definition tomographic images according to the present invention (MRI images as defined in claim 6).

The plurality of MRI images obtained by the aforementioned imaging is inputted from the MRI imaging device 24 to the computer 12, and stored in the HDD 20. Then, a three-dimensional model of a patient's model (three-dimensional brain model) is generated by the computer 12, Specifically, first, MRI images each including at least one of the three preoperative marks 80 are all selected from among the plurality of MRI images represented by the inputted data, and a three-dimensional coordinate system (hereinafter referred to as an MRI coordinate system) in which the positions of the three preoperative marks 80 on each of the selected MRI images are set as a reference (for example, any one of the three preoperative marks 80 is determined as an original point). Further, image areas corresponding to the brain of a patient's body are extracted from the plurality of MRI images, a large number of feature points which are located on the surface of the brain or at the inner side thereof and which facilitate diagnosis on the MRI image, surface measurement data, or ultrasonic tomographic image (including points which correspond to feature portions of the brain, e.g., brain grooves, gyms of brain, arteries, veins and so on, and points which correspond to the boundary between a brain tumor and a healthy portion) are set for image areas extracted from the plurality of MRI images, and the three-dimensional coordinates of each feature point in the MRI coordinate system are obtained. Then, the three-dimensional coordinates of each feature point in the MRI coordinate system, and the positions of several feature points in the MRI image are stored in the HDD 20 or the like.

Figure 4C:
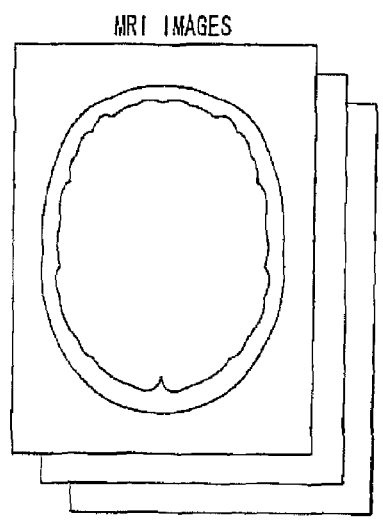
FIG. 4C is an image diagram for illustrating pickup of MRI images and generation of a three-dimensional brain model from the MRI images.
Figure 4C:
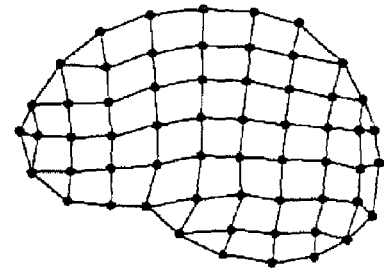

Subsequently, feature points (node points) located on the surface of the brain from among the large number of feature points as set above are connected by edge lines, and a portion enclosed by the edge lines is regarded as a flat surface. Due to this, a stereoscopic model that represents an outer edge of the brain is generated. Further, the feature points (node points) located inside the brain are also connected by edge lines, and a portion enclosed by the edge lines is regarded as a flat surface. Due to this, a stereoscopic model that represents an outer edge of the brain is divided into a large number of stereoscopic elements. As a result, as is also shown in FIG. 4C, a three-dimensional model of a patient's brain in which the patient's brain is represented as a set of a large number of stereoscopic elements can be generated from the plurality of MRI images of the head region of the patient. Further, in the computer 12, the degree of density of node points in the three-dimensional brain model is inspected based on the three-dimensional coordinates of each feature point (node point) in the MRI coordinate system, and when a region in which spaces between node points are large (i.e., a low density region) exists in the three-dimensional brain model, node points are added to this region, so as to uniform the size of stereoscopic elements constituting the three-dimensional brain model. The computer 12 allows data of the generated three-dimensional brain model to be stored in the HDD 20.

Incidentally, the aforementioned three-dimensional brain model is generated by a computer different from the computer 12, and data of the generated three-dimensional brain model may also be transferred to the computer 12.

Figure 5:
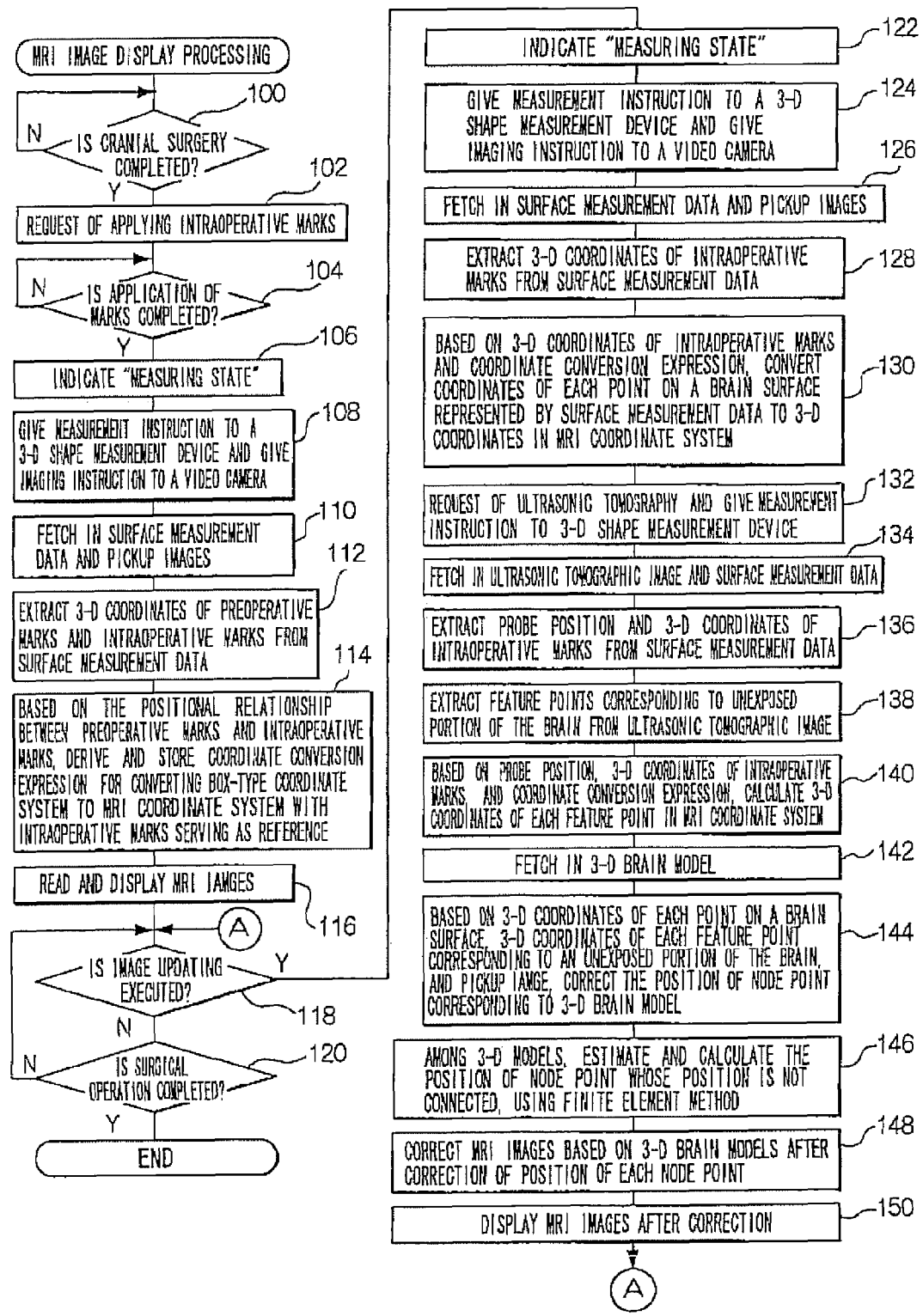
FIG. 5 is a flow chart that shows contents of MRI image displaying processing executed by a computer of a surgical operation supporting apparatus.

The surgical operation for removing a brain tumor is performed after the aforementioned pickup of MRI images and generation of the three-dimensional brain model are completed. At the start of the surgical operation, when a surgeon gives an instruction to the computer 12 to activate an MRI image display program, the MRI image display processing is executed by the computer 12 during surgery. The MRI image display processing will be hereinafter described with reference to the flow chart shown in FIG. 5.

At step 100, it is determined whether or not cranial surgery of a patient has been completed. The determination at step 100 is repeated until the decision at step 100 is made affirmative. In the brain tumor removal operations first, the scalp of a patient is cut open and the bones of skull are exposed. Thereafter, a portion of the exposed bones of skull, which portion corresponds to a previously-determined area for which cranial surgery is to be performed, is removed. Thus, the cranial surgery for exposing the brain which is an operation site is performed. When information that represents that the cranial surgery has been completed is inputted by the surgeon via the keyboard 14, the decision at step 100 is made affirmative and the process proceeds to step 102, in which the surgeon is urged to apply intraoperative marks due to, for example, a message being shown on the display 18, At step 104, it is determined whether or not application of intraoperative marks has been completed. The determination at step 104 is repeated until the decision at step 104 is made affirmative.

When the surgeon is urged to apply intraoperative marks, as is also shown in FIG. 4B for instance, the surgeon applies three or more intraoperative marks 82 on the bones of skull in the vicinity of a bone cavity formed by removing a portion of skull in the cranial surgery. As the intraoperative marks 82, spherical type white marks of 5 mm or thereabouts in diameter can be used in the same manner as the aforementioned preoperative marks 80, When application of the intraoperative marks 82 has been completed, the surgeon moves the microscope portion 38 of the surgical microscope 26 located at a position where it does not hinder the surgical operation during cranial surgery, to a position at which an exposed region of the brain comes within the visual observation field in which the objective tens 40 and the eyepiece lens 42 of the surgical microscope 26 form an optical image (accompanied with the movement of the microscope portion 38, the exposed region of the brain, intraoperative marks 32 and preoperative marks 80 come within the measurement range of the three-dimensional shape measurement device 30 and also within the image pickup range of the video camera 32), and thereafter, the surgeon inputs, via the keyboard 14, information representing that application of the intraoperative marks 82 has been completed.

As a result, the decision at step 104 is made affirmative, and in the process subsequent to step 106, calibration processing is carried out which obtains a coordinate conversion system used to convert a coordinate value in a box type coordinate system to that in the MRI coordinate system, That is to say, first, at step 106, a message indicating that the current state is a "measuring state" is shown on the display 18, whereby the surgical operation is stopped. Further, at step 108, an instruction for measurement of a surface configuration is given to the three-dimensional shape measurement device 30, and an instruction for image pickup of the surface of a brain is given to the video camera 32. As a result) in the three-dimensional shape measurement device 30, the outgoing laser light is emitted toward the patient's head including the surface of the brain, detection (calculation) of the three-dimensional coordinates of the position at which laser light is irradiated on the basis of the position at which the return laser light reflected by the head region of the patient is received by the line sensor 70 is repeated while changing the direction of the galvanometer mirror 66 (and the mirror 67) and moving the movable base 56, whereby the surface configuration of the head region of the patient, for which cranial surgery has been performed (the three-dimensional coordinates of each point in the head region including the surface of the brain) is measured. Further, the video camera 32 carries out image pickup of each part of the surface of the brain. The aforementioned measurement of the surface configuration by the three-dimensional shape measurement device 30 and image pickup of the video camera 32 are completed in 20 seconds or thereabouts.

At step 110, surface measurement data obtained by carrying out measurement of the surface configuration of the head region of a patient, for which cranial surgery has been performed, in the three-dimensional shape measurement device 30 is fetched in from the three-dimensional shape measurement device 30, and image data obtained by carrying out image pickup using the video camera 32 is fetched in from the video camera 32, At step 112, respective data corresponding to the preoperative marks 80 and respective data corresponding to the intraoperative marks 82 are extracted from the surface measurement data fetched in from the three-dimensional shape measurement device 30 (the preoperative marks 80 and the intraoperative marks 82 are detected, by the three-dimensional shape measurement device 30, as spherical type objects), and based on the extracted data, the respective three-dimensional coordinates of the center of the preoperative marks 80 and the center of the intraoperative marks 82 are obtained by calculation.

Incidentally, the preoperative marks 80 and the intraoperative marks 82 are found as a circular image area in an image obtained by image-pickup of the video camera 32, Therefore, due to the centers of the spherical type objects corresponding to the preoperative marks SO and intraoperative marks 82, which marks are represented by data extracted from the surface measurement data, and the center of circular image portions corresponding to the preoperative marks 80 and intraoperative marks 82, which marks are found in the obtained image, being caused to overlap with each other, the surface measurement data and the pickup image can be disposed in a superimposed manner. Further, the three-dimensional coordinates of each of the preoperative marks 80 are obtained before cranial surgery (before the intraoperative marks 82 are applied), and the positional relationship of the individual preoperative marks 80 indicated by the respective three-dimensional coordinates of the preoperative marks 80 calculated at step 112 (i.e., the spaces between the preoperative marks 80), and the positional relationship of the individual preoperative marks 80 obtained before the cranial surgery are compared with each other, whereby it is confirmed whether or not the positions of the preoperative marks 80 have been changed accompanied by the cranial surgery. And then, if necessary, position correction of the preoperative marks 80 and re-derivation of the respective three-dimensional coordinates of the preoperative marks 80 and the intraoperative marks 82 may also be carried out.

The three-dimensional coordinates of each of the preoperative marks 80 and intraoperative marks 82 calculated at step 112 are a coordinate value in the coordinate system, but the respective three-dimensional coordinate values of the preoperative marks 80 in the MRI coordinate system are well known. Therefore, at the next step 114, based on the positional relationship between the group of preoperative marks and the group of intraoperative marks, which is represented by the respective three-dimensional coordinates of the preoperative marks 80 and the intraoperative marks 82 calculated at step 112, and also based on the coordinate values of the preoperative marks 80 in the MRI coordinate system, a coordinate conversion expression used to convert the three-dimensional coordinate values in the box type coordinate system to the three-dimensional coordinate values in the MRI coordinate system with the positions of the intraoperative marks 82 serving as a reference, and the derived coordinate conversion expression is stored in the HDD 20 Thus: the calibration processing is completed.

In the present embodiment, the preoperative marks 80 are applied onto the scalp of the head region of a patient, and therefore, it is possibility that the positions of the preoperative marks 80 may change with the proceeding of surgery. However, the intraoperative marks 82 are applied onto the bones of skull in the vicinity of a bone cavity, thereby preventing the possibility that the positions of the intraoperative marks 82 may change during surgery, In the present embodiment, the coordinate conversion expression in which the three-dimensional coordinate values in the box type coordinate system are converted to the three-dimensional coordinate values in the MRI coordinate system with the positions of the intraoperative marks 82 serving as reference is derived as described above, and therefore, due to the aforementioned coordinate conversion expression being used, the three-dimensional coordinate values in the box type coordinate system can be converted to the three-dimensional coordinate values in the MRI coordinate system with the positions of the intraoperative marks 82 serving as reference (the MRI coordinate system with the initial positions of the preoperative marks 80 serving as reference) without being affected by the state in which the positions of the preoperative marks 80 changes with the proceeding of surgery, and it is possible to carry out high-precision positioning of the three-dimensional brain model (and the MRI images), the first position information (surface measurement data) and the second position information (unexposed area data which will be described later in detail).

Further, the three-dimensional coordinate values in the box type coordinate system can be converted to those in the MRI coordinate system with the positions of the intraoperative marks 82 serving as reference, and at the same time, in the subsequent measurement process of the three-dimensional shape measurement device 30 and in the subsequent imaging process of the video camera 32, the preoperative marks 80 applied at positions which are relatively separated from the region for which cranial surgery is performed (a bone cavity) do not need to be shown within the measurement range of the three-dimensional shape measurement device 30 and within the imaging range of the video camera 32. As a result, with the microscope portion 38 (the Three-dimensional shape measurement device 30 and the video camera 32) being moved closer to the brain, that is, an operation site, the measuring operation of the three-dimensional shape measurement device 30 and the image pickup operation of the video camera 32 can be carried out, thereby making it possible to improve the precision in the measuring operation of the three-dimensional shape measurement device 30 and in the image pickup operation of the video camera 32.

At the next step 116, the message indicative of a "measuring state" shown on the display 18 is deleted, and data of an MRI image taken before surgery is read from the HDD 20, and based on the read data, the MRI image (a high-definition tomographic image of the brain of a patient) is shown on the display 18. By referring to the aforementioned MRI image shown on the display 18, the surgeon can correctly make diagnosis of the position of a brain tumor to be removed, and so on at the stage immediately after completion of the cranial surgery. Incidentally, a high-definition display that is exclusively used to display MRI images may also be provided for displaying the MRI images. Further, but only an MRI image is shown on the display 18, but a region on which the surgeon's eyes are kept may also be clearly shown on an MRI image in such a manner that a calculation as to the center of the visual observation field in which an optical image is formed by the objective lens 40 and the eyepiece lens 42 of the surgical microscope 26 corresponds to which position on the MRI image, and a blinking mark or the like is shown at the calculated position on the MRI image.

At the stage immediately after completion of the cranial surgery, the invention is not limited to displaying of an MRI image (uncorrected MRI image) taken before surgery. In consideration of the possibility that the brain may be displaced and distorted due to the cranial surgery, even at the stage immediately after completion of the cranial surgery, an MRI image corrected through the processes of step 122 to step 150, which will be described later, may be displayed. Alternatively, at the stage immediately after completion of the cranial surgery, it may be possible for the surgeon to display an uncorrected MRI image or a corrected MRI image.

At the next step 118, it is determined whether or not a timing when the MRI image shown on the display 18 needs to be updated has come. This decision may be given by making a determination as to whether or not a fixed period of time has passed after displaying of the MRI image starts (or after previous updating of the MRI image), or by making a determination as to whether or not the surgeon has given an instruction to update the MRI image. If the decision at step 118 is made negative, the process proceeds to step 120, in which it is determined whether or not the surgical operation has been completed. This decision can be given by making a determination as to whether or not information that indicates completion of surgery has been inputted by the surgeon via the keyboard 14. If the decision at step 120 is also made negative, the process returns to step 118, and steps 118 and 120 are repeated until any one of these decisions is made affirmative.

If an MRI image is shown on the display 18 in place of the message indicative of a "measuring state", as described above, the surgeon starts the surgical operation subsequent to the cranial surgery in the surgical removal of a brain tumor. This surgical operation includes operations for pressing the brain using a scoop, cutting open or removing a part of the brain, and so on. When these operations are applied to the brain, various parts of the brain are displaced or distorted. Therefore, the actual state of the brain (the position or shape of various parts) becomes different from the state of the brain represented by the MRI image shown on the display 18. Thus, even if the MRI image shown on the display 19 is referred to, it becomes difficult for the surgeon to make a precise diagnosis of the position or range of the brain tumor to be removed. Accordingly, in the MRI image displaying processing, if a fixed period of time has passed after displaying of the MRI image starts (or after previous updating of the MRI images is performed), or if the information that gives an instruction to update the MRI image is inputted by the surgeon via the keyboard 14, the decision at step 120 is made affirmative and the process proceeds to step 122. In the process subsequent to step 122, processing for correcting and updating the MRI images shown on the display 18 is carried out.

In other words, first, at step 122, the message indicating that the current state is a "measuring state" is shown on the display 18, and the surgical operation is thereby stopped. Further, at step 124, an instruction is given to the three-dimensional shape measurement device 30 to measure the surface configuration, and an instruction is given to the video camera 32 to take an image of the surface of a brain. As a result, in the three-dimensional shape measurement device 30, the outgoing laser light is emitted toward a patient's brain including the surface of the brain, and detection (calculation) of the three-dimensional coordinates of the position at which laser light is irradiated, based on the position at which the return laser light reflected by the brain of a patient is received by the line sensor 70, is repeated while changing the direction of the galvanometer mirror 66 (and the mirror 67) and moving the movable base 56. Thus, the measuring operation of the surface configuration of the head region of the patient, for which the cranial surgery has been performed (the three-dimensional coordinates of each of points in the head region) is carried out. Further, the video camera 32 carries out an image pickup operation for the surface of the brain. The aforementioned measuring operation of the surface configuration by the three-dimensional shape measurement device 30 and the image pickup operation of the video camera 32 are completed in approximately 20 seconds.

Incidentally, in the surgical removal of a brain tumor is performed in such a manner that the surgeon moves the microscope portion 38 by holding the grip portion 46 of the surgical microscope 26, and visually recognizes a region targeted for the surgical operation. The three-dimensional shape measurement device 30 and the video camera 32 are mounted on the surgical microscope 26, and therefore, when the surface configuration is measured by the three-dimensional shape measurement device 30 or the image pickup operation is carried out by the video camera 32, it is not necessary to further adjust the measurement range of the surface configuration or the image pickup range. The three-dimensional shape measurement device 30 allows measurement of the surface configuration within the measurement range including the surface of the brain and the intraoperative marks 82 only by carrying out measurement of the surface configuration for a fixed range in the box type coordinate system. Further, the video camera 32 also allows imaging of an image pickup range including the surface of the brain and the intraoperative marks 82 only by carrying out pickup of images for a fixed image pickup range.

At step 126, the surface measurement data obtained by measurement of the three-dimensional shape measurement device 30 is fetched in from the three-dimensional shape measurement device 30, and image data obtained by image pickup of the video camera 32 is fetched in from the video camera 32. At step 128, data corresponding to the individual intraoperative marks 82 is extracted from the surface measurement data fetched in from the three-dimensional shape measurement device 30, and based on the extracted data, the three-dimensional coordinates of the center of the intraoperative marks 82 are obtained by calculation. At step 130, the coordinate conversion expression derived at the previous step 114 is read out from the HDD 20, and by using the read coordinate conversion expression, the three-dimensional coordinates of each of points on the surface of the brain, which points are represented by the surface measurement data (the coordinate values in the box type coordinate system) are converted to the three-dimensional coordinate values in the MRI coordinate system, respectively, with the positions of the intraoperative marks 82 represented by the three-dimensional coordinates obtained at step 128 serving as references, and the surface measurement data after the coordinate conversion is stored in the HDD 20. As a result, alignment of the first position information (surface measurement data) and the three-dimensional brain model (and the MRI image) is completed.

At step 132, due to a message that gives an instruction to the surgeon to produce ultrasonic tomographic images being shown on the display 18, the ultrasonic tomographic images of the brain are produced by the ultrasonic tomographic device 34, and an instruction for measurement of the surface configuration is given to the three-dimensional shape measurement device 30. As a result, the operator holds the probe 36, and gives an instruction to the ultrasonic tomographic device 34 to produce ultrasonic tomographic images with the leading end of the probe 36 being directed toward the brain of the patient.

When an instruction for pickup of ultrasonic tomographic images is given, in the ultrasonic tomographic device 34, the operation of transmitting ultrasonic waves from the leading end of the probe 36, converting an electric signal outputted from the probe 36 in accordance with the ultrasonic waves reflected by an arbitrary object and received by the probe 36, to digital data, and further causing the data to be stored in memory or the like is carried out in a repeated manner while changing the outgoing direction of the ultrasonic waves from the leading end of the probe 36 along a fixed direction, and thereafter, the data stored in the memory or the like is reordered, thereby allowing generation of data that represents an ultrasonic tomographic image of the brain for a cross-section parallel to the aforementioned fixed direction, Further, the surgeon repeatedly gives an instruction to the ultrasonic tomographic device 34 to produce ultrasonic tomographic images, while moving the probe 36 by a substantially fixed distance at a time in a direction substantially orthogonal to the aforementioned fixed direction.

As a result, a plurality of ultrasonic tomographic images corresponding to plural cross-sections apart from one another substantially at regular intervals are respectively taken for the brain of a patient. The operation of taking a plurality of ultrasonic tomographic images is completed in approximately three minutes. Further, during the operation of taking ultrasonic tomographic images corresponding to various cross-sections as described above, due to the surface configuration being continuously measured by the three-dimensional shape measurement device 30, the position of the probe 36 (three-dimensional coordinates of the marks 36A attached to the probe 36), and the positions of the intraoperative marks 82 are repeatedly measured.

At step 134, data of a plurality of ultrasonic tomographic images taken by the ultrasonic tomographic device 34 is fetched in from the ultrasonic tomographic device 34, and the surface measurement data obtained by measurement of the three-dimensional shape measurement device 30 is fetched in from the three-dimensional shape measurement device 30. At step 136, data corresponding to each of the marks 36A of the probe 36 at the time of taking each ultrasonic tomographic image, and data corresponding to each of the marks 82 are respectively extracted from the surface shape measurement data fetched in from the three-dimensional shape measurement device 30, and based on the extracted data, the three-dimensional coordinates of the center of each of the marks 36A at the time of taking each ultrasonic to tomographic image, and the three-dimensional coordinates of the center of each of the intraoperative marks 82 are respectively obtained by calculation. Further, based on the three-dimensional coordinates of the center of each of the marks 36A at the time of taking each ultrasonic tomographic image, the three-dimensional coordinates (coordinate values in the box type coordinate system) at the leading end of the probe 36 at the time of taking each ultrasonic tomographic image, and the direction of the probe 36 (the direction thereof in the box type coordinate system) are calculated.

At step 138, based on data of the plurality of ultrasonic tomographic images fetched in from the ultrasonic tomographic device 34, feature points (including points corresponding to feature portions of a brain, such as brain grooves, arteries, veins and so on, and also including points corresponding the boundaries between a brain tumor and a healthy portion), which feature points are located within the brain (an unexposed portion in which the three-dimensional coordinates can be detected by the three-dimensional shape measurement device 30) and are readily recognized on an image, are respectively extracted from each of ultrasonic tomographic images. At step 140, first, based on the three-dimensional coordinates at the leading end of the probe 36 at the time of taking each ultrasonic tomographic image, and the direction of the probe 36, both of which are calculated in step 136, and also based on the positions of the feature points on each of the ultrasonic tomographic image, the three-dimensional coordinate of each feature point in the box type coordinate system are calculated. Subsequently, the coordinate conversion expression derived at the previous step 114 is read out from the HDD 20, and using the coordinate conversion expression read therein, the three-dimensional coordinates of each feature point in the box type coordinate system are converted to the three-dimensional coordinate values in the MRI coordinate system with the various intraoperative marks 82 represented by the three-dimensional coordinates obtained at step 136, and the three-dimensional coordinates of each feature point after having been subjected to the coordinate conversion, and the position of each feature point on the ultrasonic tomographic image are stored, as unexposed area data, in the HDD 20. As a result, alignment of the second position information (unexposed area data), and the three-dimensional brain model (and the MRI image) is completed.

When, due to the aforementioned processing, acquisition of surface measurement data used for correction of an MRI image, and unexposed area data has been completed, at the next step 142, data of a three-dimensional brain model (also refer to FIG. 6A) is fetched in from the HDD 20. At the subsequent step 144, matching between a produced image and an MRI image (a determination that each of points of the brain surface represented on the produced image corresponds to which portion on the MRI image) is carried out by collating the feature portion of the brain appearing on the produced image represented by image data fetched in from the video camera 32 (for example, brain grooves, gyms of a brain, arteries, veins and so on) with the feature portions of the brain appearing on the MRI image. Further, in the present embodiment, the position and direction of the video camera 32 are adjusted so as to allow image pickup of the same range as the measurement range of the three-dimensional shape measurement device 30. Therefore, based on the result of matching between the produced image and the MRI image, it is determined that each of the points of the brain surface in which the three-dimensional coordinates in the MRI coordinate system are well known by the surface measurement data correspond to which portion on the MRI image. And then, by determining, based on the positions of the node points (feature points) of the three-dimensional brain model stored in the HDD 20 at the time of generating the three-dimensional brain model, a node point corresponding to each point on the surface of the brain in which the three-dimensional coordinates in the MRI coordinate system are well known by the surface measurement data; matching between the surface measurement data and the three-dimensional brain model is carried out.

As described above, due to the image obtained by the video camera 32 being used for the matching between the surface measurement data and the three-dimensional brain model, the matching between the surface measurement data and the three-dimensional brain model can be carried out by using, for example; features which are not clear on the surface measurement data such as change of color in the surface of a brain. Therefore, the precision of matching between the surface measurement data and the three-dimensional brain model can be improved.

Further, at step 144, due to the feature portions of the brain represented by an ultrasonic tomographic image being collated with the feature portions of the brain represented by the MRI image in a manner similar to the above, it is determined that points corresponding to the inside of the brain in the ultrasound tomographic image correspond to which portion on the MRI image, and based on the positions of the node points (feature points) of the three-dimensional brain model on the MRI image, and the positions of feature points extracted from the ultrasonic tomographic image on the ultrasonic tomographic image, a node point corresponding to each of feature points within the brain in which the three-dimensional coordinates in the MRI coordinate system are well known by the unexposed area data from among various node points constituting the three-dimensional brain model.

Due to the three-dimensional coordinates of the node point which is determined as that corresponds to any of the points on the brain surface represented by the surface measurement data being replaced by three-dimensional coordinates of the corresponding point (the three-dimensional coordinates in the MRI coordinate system represented by the surface measurement data), and also due to the three-dimensional coordinates of the node point which is determined as that corresponds to any of the feature points within the brain represented by the unexposed area data being replaced by the three-dimensional coordinates of the corresponding feature point (the three-dimensional coordinates in the MRI coordinate system represented by the unexposed area data), as is also shown in FIG. 6B for instance, the position of the node point corresponding to any one of the points on the brain surface represented by the surface measurement data or any one of the feature points within the brain represented by the unexposed area data is corrected, from among the node points constituting the three-dimensional brain model. Incidentally, FIG. 6B shows an example in which the position correction is carried out only for node points corresponding to the front surface or rear surface of the brain, but node points corresponding to a region between the front and rear surfaces of the brain may also be intended for the correction of the positions thereof.

At step 146, due to, based on the node points intended for correction of the positions thereof and the corrected positions of the node points at step 144, external force that causes the node points targeted for correction of the positions thereof at step 144, from among the node points constituting the three-dimensional brain model, to move to the corrected positions at step 144 being applied to the three-dimensional brain model, the way in which the positions of other node points are displaced is estimated and calculated by applying a finite element method, and based on the result of the estimation and calculation, as also shown in FIG. 6C for instance, the positions of node points other than the node points targeted for correction of the positions thereof at step 144 are corrected. As a result, the three-dimensional brain model can be corrected so as to represent the current state of the brain (displacement or distortion of each of the parts thereof) with a high degree of precision. Incidentally, a method similar to the finite element method (for example, a simplified method of the finite element method, which is intended for high speed processing and the like) may also be applied in place of the finite element method.

At the subsequent step 148, based on the three-dimensional brain model in which the positions of the node points are corrected at steps 144 and 146, and the positions of the node points (feature points) of the three-dimensional brain model on the MRI image, Geometrical conversion is carried out for the MRI image so as to, for examples allow the positions of pixels of the MRI image to move in accordance with the movement of the positions of the node points based on the correction of the three-dimensional brain model, whereby the MRI image is corrected depending on the displacement or distortion of various parts of the brain represented by the corrected three-dimensional brain model. As a result, a high-definition MRI image that represents the current state of the brain with a high degree of precision can be obtained.

As a result, by referring to the aforementioned MRI images updated and shown on the display 18, the surgeon can make a correct diagnosis of the position of a brain tumor to be removed, and the like even if the parts of a brain are displaced or distorted due to various surgical operations after cranial surgery. Further, the aforementioned correction and update/display of MRI images are carried out repeatedly (each time the decision of step 118 is made affirmative) until the surgical operation is finished (until the decision of step 120 is made affirmative), Therefore, the surgeon can perform the surgical operation, by referring to the MRI images which are updated and displayed as needed, while confirming a proper anatomical positional relationship between the region for which the surgical operation has been performed, and a peripheral brain region at various stages, for example, at the time when removal of the brain tumor is started, or at the time when the removal operation is completed. Further, the presence of a remaining-tumor (rest of the tumor) can be confirmed, thereby making it possible to completely remove the brain tumor to be removed. Moreover, the MRI image shown on the display 18 may be a functional mapping MRI image in which the distribution state of various functional fields as searched in advance is indicated as a map in a superimposed manner. However, when the functional mapping MRI image is displayed, the surgeon can proceed with the surgical operation while keeping track of the position relationship between the region for which the surgical operation is performed, and each of the functional fields.

Industrial Applicabilty

In this manner, in the surgical operation supporting apparatus 10 according to the present embodiment, based on the surface configuration data obtained by optically measuring the surface of a brain using the three-dimensional shape measurement device 30 during surgery (and by carrying out image pickup of the surface of the brain using the video camera 32 during surgery), and unexposed area data obtained by measuring an unexposed area of the brain with ultrasonic waves by means of the ultrasonic tomographic imaging device 34 during surgery, an MRI image as previously picked up is corrected and the correct MRI image that represents the current state of the brain with a high degree of precision is displayed during the surgical operation, Accordingly, it is possible for the surgeon to recognize the current state of the brain (the state of the brain after displacement or distortion occurs during the surgical operation and so on), and realize improvement in the precision of the surgical operation.

Further, in the surgical operation supporting apparatus 10 according to the present embodiment, the operation of measuring the surface configuration using the three-dimensional shape measurement device 30 and the image pickup operation of the video camera 32 are completed over 20 seconds or thereabouts and the image pickup operation of a plurality of ultrasonic tomographic images using the ultrasonic tomographic device 34 is completed over 3 seconds or thereabouts, Therefore, compared with the case in which MRI images are periodically taken during the surgical operation, the downtime of the surgical operation is significantly reduced. Accordingly, it is possible to avoid the situation in which the surgical operation is interrupted due to MRI images which represent the actual state of the brain being displayed during the surgical operation.

Moreover, the surgical operation supporting apparatus 10 according to the present invention can be realized only by adding the three-dimensional shape measurement device 30, the video camera 32, and the computer 12 having a three-dimensional model generation pro-ram and an MRI image display program installed thereon. Therefore, compared with the case in which MRI images are periodically taken during surgery, an apparatus of far less cost can be realized.

In the foregoing, the structure in which only one video camera 32 is provided was described above, but the present invention is not limited to the same. A plurality of video cameras used for carrying out image pickup from different directions may be provided, and due to images produced by these video cameras being used to carry out matching between surface measurement data and a three-dimensional brain model, the precision of matching between the surface measurement data and the three-dimensional brain model may be further improved.

Further, there was shown above a case in which the present invention is applied to supporting of a surgical operation for removing a brain tumor, but the present invention is not limited to the same and may also be applied to any surgical operation of the brain other than that for removing the brain tumor. Further, the operation site is not limited to the brain region, and the present invention is also applicable to supporting of a surgical operation for any body part.

Moreover, there was described above a case in which an MRI image is used as a high-definition tomographic image according to the present invention. However, any tomographic image that represents an operation site with a high degree of definition may be applied, for example, tomographic images produced by using other known image pickup method such as X-ray CT imaging or the like. Further, when a surgical operation is performed while referring to other tomographic images produced by other image pickup methods (for example, positron emission tomography (PET) or single photon emission computer tomography (SPECT)) in addition to the high-definition tomographic image according to the present invention, the other tomographic images are previously made to correspond to the high-definition tomographic images according to the present invention, and after the high-definition tomographic images according to the present invention are corrected based on the surface measurement data and unexposed area data as described above, the aforementioned other tomographic images may also be corrected and displayed based on the corrected high-definition tomographic images.

Explanation of Reference Numerals 10 surgical operation supporting apparatus
12 computer
18 display
22 drive
24 MRI imaging device
26 surgical microscope
30 three-dimensional shape measurement device
32 video camera
34 ultrasonic tomographic device
36 probe
80 preoperative mark
82 intraoperative mark

What is claimed is:

1. A surgical operation supporting apparatus comprising:
first acquisition means for optically measuring a surface of an operation site during surgery and acquiring first position information representing a three-dimensional position of each of points on the surface of the operation site;
second acquisition means for:
measuring an unexposed portion of the operation site with ultrasonic waves during surgery, the unexposed portion of the operation site being below the surface of the operation site; and
acquiring second position information representing a three-dimensional position of each of points in the unexposed portion of the operation site;
correction means for, based on the first position information acquired by said first acquisition means and the second position information acquired by said second acquisition means, correcting a position of a portion whose three-dimensional position is known by the first position information and the second position information in a generated three-dimensional model of the operation site, the generated three-dimensional model comprising a plurality of node points each corresponding a different point having a particular position in the unexposed portion, and thereafter, estimating displacement and distortion at a portion whose three-dimensional position is not known in the generated three-dimensional model based on a plurality of high-definition tomographic images of the operation site to obtain an estimated result, such images are taken before surgery and comprise a plurality of pixels having an initial position, re-correcting the three-dimensional model of the operation site by use of a finite element method and the estimated result, and correcting the plurality of high-definition tomographic images by automatically moving at least some of the plurality of pixels from the initial position to a different position in accordance with movement of each particular position of one or more of the plurality node points in the re-corrected three-dimensional model of the operation site; and
display control means for allowing the high-definition tomographic images corrected by said correction means to be shown on a display.

2. The surgical operation supporting apparatus according to claim 1, wherein said first acquisition means comprises a scanning device mounted at a surgical microscope and scanning the surface of the operation site with laser light, and detecting means mounted at the surgical microscope and receiving laser light reflected by the surface of the operation site, thereby detecting a three-dimensional position of a portion on which the laser light is irradiated, on the surface of the operation site, and an operation of detecting the three-dimensional position by said detecting means is carried out repeatedly while scanning each of the points on the surface of the operation site with laser light, thereby acquiring the first position information.

3. The surgical operation supporting apparatus according to claim 1, wherein said first acquisition means further comprises image pickup means mounted at the surgical microscope and producing images of the surface of the operation site, and said correction means is provided so as to estimate displacement and distortion at each of the points in the operation site also using images produced by said image pickup means.

4. The surgical operation supporting apparatus according to claim 1, wherein said second acquisition means comprises a probe that transmits ultrasonic waves to the operation site and receives ultrasonic waves reflected by the points in the unexposed portion of the operation site, and conversion means that converts the ultrasonic waves received by the probe to tomographic images, and said second acquisition means is provided so as to acquire the second position information by obtaining the three-dimensional position of each of the points on the ultrasonic tomographic images obtained by said conversion means.

5. The surgical operation supporting apparatus according to claim 4, wherein:
said first acquisition means comprises a scanning device mounted at a surgical microscope and scanning the surface of the operation site with laser light and detecting means mounted at the surgical microscope and receiving laser light reflected by the surface of the operation site, thereby detecting a three-dimensional position of a portion on which the laser light is irradiated, on the surface of the operation site, and said first acquisition means also detects the three-dimensional position of the probe of said second acquisition means; and
said second acquisition means obtains, based on the three-dimensional position of the probe detected by said first acquisition means, the three-dimensional position of each of the points on the ultrasonic tomographic image.

6. The surgical operation supporting apparatus according to claim 1, wherein operation of acquiring the first position information by said first acquisition means, acquiring the second position information by said second acquisition means, correcting the plurality of high-definition tomographic images by said correction means, and displaying the high-definition tomographic images by said display is carried out repeatedly during the surgical operation.

7. A surgical operation supporting method comprising:
a first step in which, based on a plurality of high-definition tomographic images of an operation site taken as an image before surgery, a three-dimensional model of the operation site is generated;
a second step in which a surface of the operation site is optically measured during surgery, so as to acquire first position information that represents a three-dimensional position of each of points on the surface of the operation site, and an unexposed portion of the operation site is measured with ultrasonic waves during surgery, so as to acquire second position information that represents a three-dimensional position of each of points of the unexposed portion in the operation site, the unexposed portion of the operation site being below the surface of the operation site;
a third step in which, based on the first position information and the second position information acquired by said second step, a position of a portion whose three-dimensional position is known by the first position information and the second position information in the three-dimensional model of the operation site is corrected, wherein the three-dimensional model comprising a plurality of node points each corresponding a different point having a particular position in the unexposed portion, and thereafter, displacement and distortion at a portion whose three-dimensional position is not known in the three-dimensional model is estimated based on a plurality of high-definition tomographic images of the operation site to obtain an estimated result, such images are taken before the surgery and comprise a plurality of pixels having an initial position, the three-dimensional model of the operation site is re-corrected by use of a finite element method and the estimated result, and the plurality of high-definition tomographic images of the operation site are corrected by automatically moving at least some of the plurality of pixels from the initial position to a different position in accordance with movement of each particular position of one or more of the plurality node points in the re-corrected three dimensional method of the operation site; and
a fourth step in which the high-definition tomographic images corrected by said third step are shown on a display.

8. A non-transitory computer readable storage medium comprising instructions, which when executed by a processor, cause the processor perform the following operations:
measuring a surface of an operation site during surgery to acquire first position information representing a three-dimensional position of each of points on the surface of the operation site at a scanning device;
measuring an unexposed portion of the operation site with ultrasonic waves generated by a probe during the surgery, the unexposed portion of the operation site being below the surface of the operation site, and acquiring second position information representing a three-dimensional position at each of points in the unexposed portion of the operation site at via the probe;
correcting at a computer a position of a portion whose three-dimensional position is known by the first position information and the second position information in a generated three-dimensional model of the operation site, the generated three-dimensional model comprising a plurality of node points each corresponding a different point having a particular position in the unexposed portion;
estimating at the computer, based on the first position information acquired by the scanning device and the second position information acquired by the probe, the displacement and distortion at a portion whose three-dimensional position is not known in the generated three-dimensional model based on a plurality of high-definition tomographic images obtained before the surgery to obtain an estimated result, the plurality of high-definition tomographic images comprising a plurality of pixels having an initial position;
re-correcting the generated three-dimensional model of the operation site by use of a finite element method and the estimated result; and
correcting the plurality of high-definition tomographic images of the operation site by automatically moving at least some of the plurality of pixels from the initial position to a different position in accordance with movement of each particular position of one or more of the plurality node points in the re-corrected three-dimensional model; and generating at a display means the high-definition tomographic images corrected based on the re-corrected three-dimensional model.

9. The non-transitory computer readable storage medium of claim 8, wherein correcting the plurality of high-definition tomographic images comprises:

geometrically converting the plurality of high-definition tomographic images of the operation site to correct the plurality of high-definition tomographic images based on the re-corrected three-dimensional model.

10. The non-transitory computer readable storage medium of claim 8, wherein the operation site is a brain, and each of points in the unexposed portion are located within the brain.

* * * * *